United States Patent [19]

Rawls et al.

[11] Patent Number: 5,527,181
[45] Date of Patent: Jun. 18, 1996

[54] SHAPE-CONFORMING DENTAL WEDGES

[75] Inventors: H. Ralph Rawls, San Antonio; Jerry W. Nicholson, Boerne, both of Tex.

[73] Assignee: Board of Regents, The University of Texas System, Austin, Tex.

[21] Appl. No.: 199,629

[22] Filed: Feb. 22, 1994

[51] Int. Cl.⁶ ............................. A61C 7/00; A61G 17/02
[52] U.S. Cl. .................. 433/149; 433/80; 433/39; 433/136
[58] Field of Search ..................... 433/80, 148, 149, 433/136, 39

[56] References Cited

U.S. PATENT DOCUMENTS

| | | | |
|---|---|---|---|
| 309,709 | 12/1884 | Genese | 433/149 |
| 2,782,503 | 2/1957 | Thompson | 433/149 X |
| 2,867,905 | 1/1959 | Meacham. | |
| 3,473,226 | 10/1969 | Arlers et al.. | |
| 3,890,714 | 6/1975 | Gores | 433/149 |
| 4,020,558 | 5/1977 | Cournut et al. | 433/80 |
| 4,175,326 | 11/1979 | Goodson | 433/80 |
| 4,259,070 | 3/1981 | Soelberg et al. | 433/149 |
| 4,337,041 | 6/1982 | Harsany | 433/149 |
| 4,696,646 | 9/1987 | Maitland | 433/149 |
| 4,715,816 | 12/1987 | Mogelof | 433/149 |
| 4,764,377 | 8/1988 | Goodson | 433/80 X |
| 4,986,752 | 1/1991 | Graves | 433/138 |

FOREIGN PATENT DOCUMENTS

8912620 U   1/1990   Germany ................. A61C 5/04

*Primary Examiner*—Nicholas D. Lucchesi
*Attorney, Agent, or Firm*—Arnold, White & Durkee

[57] ABSTRACT

A one-piece dental wedge comprised of a rigid core and an elastic outer component. Both the core and the outer component are comprised of biocompatible materials. The core may be comprised of a plastic, like a polymethyl methacrylate resin, wood, metal, or the like. The elastic outer component is comprised of an elastomer of either the gel or non-gel type.

18 Claims, 3 Drawing Sheets

SHAPE-CONFORMING DENTAL WEDGES

FIELD OF THE INVENTION

The present invention relates generally to the field of dental instruments and more particularly to dental wedges.

DESCRIPTION OF THE RELATED ART

The art of restorative dentistry has been practiced for centuries. Technological advancement in the art has been particularly rapid in the past 50 years. The instruments and materials used to restore the human dentition have been improved and new materials developed, such that the present art of restorative dentistry barely resembles the practices of 25 years ago. However, one thing has not changed. When the human dentition is damaged due to trauma or decay such that the interproximal surfaces of the teeth (the surfaces in between the teeth) are involved, a matrix band and dental wedge are still employed to aid in the restoration of the teeth.

Dental wedges are well known in the art and have been used in restorative dentistry for over a century. Generally, dental wedges are used to separate the teeth and hold a matrix band against the side of the tooth while a restoration is being placed. These functions are important for the successful restoration of the form and function of the tooth being restored. Unless adequate separation of the teeth is achieved, the adjacent teeth, once restored, will not contact one another or will do so only very lightly. Without adequate contact between the teeth, food will pack and otherwise accumulate in between the teeth, leading to decay and periodontal (gum) problems. And, unless the matrix band conforms adequately to the side of the tooth, filling material can be forced below the gum line or leave the tooth with unnatural and irregular contours known as ledges, overhangs and underhangs. These flaws aid and cause plaque accumulation, leading to decay and periodontal problems.

Generally, the ideal dental wedge should be relatively hard in order to drive the teeth apart at least the thickness of the average matrix band (approximately 0.002 inch). When the wedge and matrix band are removed, the restored teeth should rebound to their normal physiologic position in order to maintain physiologic contact and prevent food debris from packing between the teeth during chewing. The wedge should also provide resistance against the matrix band so as to prevent deformation or dislodgment due to the outward pressure the dentist applies when packing restorative materials in the matrix-confined cavity space.

Most dental wedges are of a basic tetrahedral shape and taper to a point. In use, a wedge is inserted into the space between the adjacent teeth at the gum line and forced into the space to force separation of the teeth so that they may be restored. The amount of separation achievable with a wedge depends upon several factors. The interdental space present between the adjacent teeth and the size of the wedge are probably the most important of those factors.

Most commercially available dental wedges have been of the basic tetrahedral shape and made of various types of wood. To accommodate different sizes of interdental spaces, wedges are generally available in various sizes from small to large and the size used determined by the size of the interdental space. These wedges achieve the requirement that the wedge be hard enough to allow the teeth to be driven apart. However, wooden wedges suffer from the problem of not conforming adequately to the interproximal surface of the tooth and from having a tendency to "back out" of the interdental space once having been placed. This tendency for the wedge to "back out" or not stay in its activated position tends to defeat the purpose of using the wedge in the first place. That is, if the wedge "backs out," the separation of the teeth is lost and the matrix band is no longer supported against the side of the tooth, allowing for restorations with overhangs and poor interproximal contacts.

Dental wedges generally have been made of various hard materials and have focused on the tooth separation function of the dental wedge. Indeed, virtually all of the wedges of the prior art have focused on separating the teeth to be restored. These wedges have generally achieved tooth separation, but most of them have also had a tendency to "back out."

Another basic requirement of a dental wedge is that it be able to cause the matrix band to intimately conform to the anatomical surfaces of the tooth to be restored. Often, the interproximal surface of a tooth will be concave. Wherever a dental wedge does not intimately contact the flexible matrix band and force it against the concave surface of the tooth, the band is unsupported. In such a condition, a gap or opening will develop in response to the pressure of packing the restorative material into the matrix-confined cavity preparation. These gaps allow the filling material to push past the matrix and create a ledge, overhang, or an otherwise unacceptable contour of the tooth in the interdental space. Thus, rigid, fixed-shape wedges or wedge-type devices cannot adapt well to the variable contours of the interproximal spaces.

There have been varied attempts to compensate for a rigid, fixed-shape wedge design by incorporating convex contours into a polystyrene dental wedge, by using a thermoplastic coating on a lemon wood dental wedge, or by using various plastic formulations to create a dental wedge. None of these attempts have met the ideal criteria of providing both of the basic functions of a dental wedge, i.e., spreading the teeth and conforming the matrix band to the irregular contours of the side of the tooth.

Plastics in general are unacceptable materials for a wedge meeting both of the above criteria because of their tendency to flow with resulting permanent, non-recoverable deformation. Thus, once a plastic dental wedge has been deformed by being forced into an interdental space, the wedge is deformed and does not have the memory to "rebound" into the concave surface of the side of the tooth.

SUMMARY OF THE INVENTION

The present invention provides a one-piece dental wedge which is capable of both separating adjacent teeth and conforming a matrix band to the irregular surfaces of a tooth being restored, and doing so without "backing out." To meet the criterion of conforming the matrix band to the irregular contour of the side of the tooth, the wedge of the invention possesses elastic properties which enable it not only to recover from deformation but also "rebound" into the irregular contours of the side of the tooth. The elasticity enables the wedge to be forced between two teeth and then expand into a concave, interproximal defect in one of the teeth with enough force to cause a matrix band to adapt to the interproximal contours.

The present invention in a general aspect comprises a one-piece dental wedge which includes a rigid core and an outer layer of an elastic material which is bonded or otherwise coupled or joined to the core. The elastic material must be firm enough to provide resistance to compression when wedged between two teeth, but also capable of rebounding from compression to conform to the contours of tooth surfaces. In one preferred embodiment, the invention is comprised of a rigid core having a tetrahedral shape and an elastic component fused over the rigid core. The elastic component of the wedge is selected to deform when forced between teeth, but then rebound into the irregular contours of the sides of the teeth.

DETAILED DESCRIPTION OF THE PREFERRED EMBODIMENTS

Figure 1:
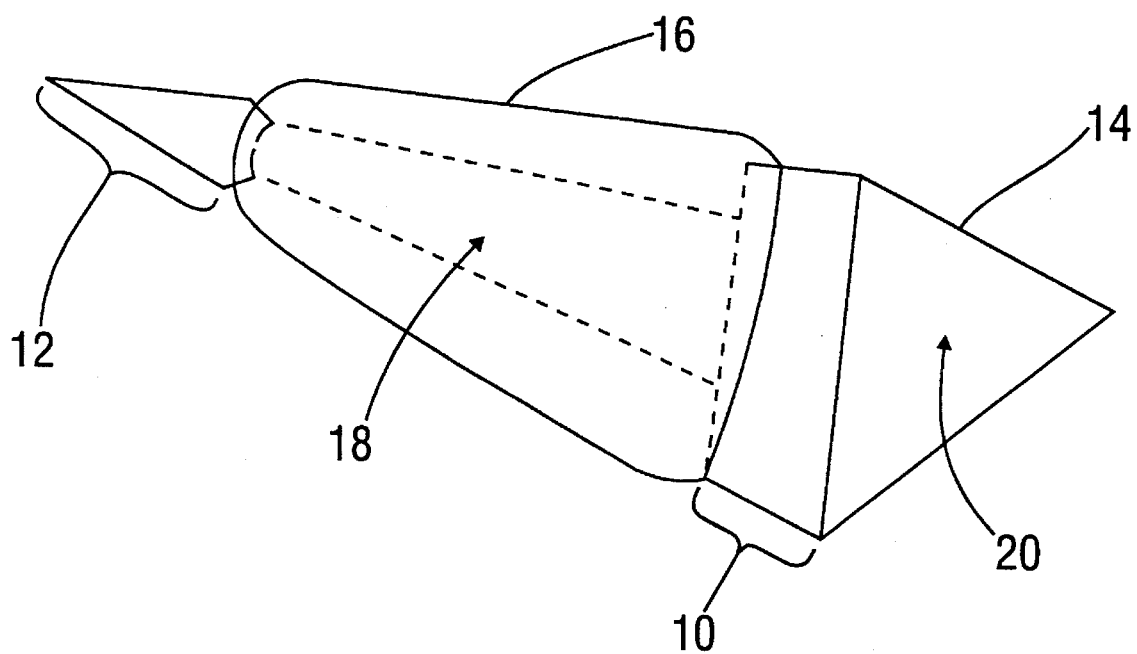
FIG. 1 is a perspective view of a preferred embodiment of the present invention.

A dental wedge of the present invention is illustrated in FIG. 1. In a preferred embodiment, the dental wedge has an overall tetrahedral shape tapering from a butt end portion 10 to a pointed tip portion 12 at the opposite end. Those skilled in the art will recognize, however, that other wedge cross-sections may be used. Thus, wedges having more than three side surfaces, or even a conical geometry, may be employed. The dental wedge of the present invention is comprised of two principal components: a rigid core component 14 and an elastic outer component 16. The outer component is fused, cemented, frictionally fitted or otherwise fixed to the core to form a unitary structure. In general, the rigid core and the overall wedge preferably have similar cross-sections.

The core of FIG. 1 forms a butt end portion 10, a body portion 18 to which the elastic outer component 16 is fused, and a pointed tip portion 12. The butt end portion of the core 10 has a transverse flat surface 20 which is designed to be engaged by a suitable tool for easy placement of the dental wedge into the interproximal space.

The core component of the invention, especially the body portion 18, is preferably hard and large enough to support the elastic outer component 16 and thus achieve adequate tooth separation. Further, the core is sufficiently rigid to aid in placement of the wedge when force is applied to the butt end of the wedge during placement. A flexible core may not allow an operator to achieve necessary separation.

The material comprising the core component of the invention should be compatible with the material comprising the elastic outer component such that the two components will not separate during use. Further, both the core component and the elastic outer component must be biocompatible, i.e., compatible with human oral tissues.

An especially preferred material for the core component has been found to be polymethyl methacrylate resin. Other biocompatible materials may also be suitable, for example other plastics, wood, metal, or other synthetic materials. Plastics that are not suitable to use for the outer surface of dental wedges are often sufficiently strong and rigid enough to serve as the core components of the wedges of the invention.

The outer component is preferably a synthetic elastomer which is capable of being fused or otherwise fixed to the core. It is preferably sufficiently hard enough to cause separation of the teeth; however, it must also be sufficiently soft and elastic to expand and conform to the side wall surfaces of the tooth.

A key feature of the present invention is the use of elastomers as the elastic, deformable component of the wedge. For purposes of the present invention, "elastomer" is used to mean materials having elastic properties, thus having an elastic memory to return the material to its original shape after being deformed. Elastomers generally have rubber-like properties and for purposes of the present invention may be classified as "gel" or "non-gel" type.

A gel is a colloidal solution in which the disperse phase has combined with the continuous phase to produce a swollen, viscous, jelly-like structure. An elastomer of the gel type, for purposes of the present invention may also comprise a disperse phase which may be some form of filler, generally a collodial silica, quartz, amorphous silica or glass, and a continuous phase, which may be a liquid solvent, for example water.

Gels may be further classified by the solvent used to form the gel. Hydrogels are gels wherein the solvent is water. Alcohols or other organic solvents may also be used as swelling agents to form a gel useful in the present invention.

Elastomers of the non-gel type, for purposes of the present invention, are primarily natural or synthetic polymers such as the rubbers of polyisoprene, polybutadiene, polyethers, polysiloxanes, silicones and polysulfides. Generally, the rigidity of these polymers varies with the degree of cross-linking of the polymer chains. The higher the degree of cross-linking the more rigid the resulting polymeric structure.

As used herein, the term "hydrogel" comprises a polymer such as a copolymer of hydroxyethyl methacrylate ("HEMA") and hydroxypropyl methacrylate ("HPMA") or a copolymer of HEMA and trimethylamino ethylmethacrylate chloride ("TMAEM-Cl") with triethylene glycol dimethacrylate ("TEGDMA") as a cross-linker, together with an aqueous solvent.

For purposes of this invention, elastomers possessing a hardness in the range of a hard rubber (about 50 or more on the durometer-A scale) are preferred. The performance of the dental wedge of the present invention is dependent upon both the hardness (resistance to indentation) and the resilience (ability to recover from indentation) of the elastomer. The function of the core, however, cannot be overlooked. The core must be rigid enough to support the deformable component and to force the separation of the teeth. Without the rigid core, the wedge, as a unit, may not achieve proper separation.

It is contemplated that a wedge of the present invention may be made entirely of elastomeric materials. The core and outer component may be made from the same material but with different filler loadings (of, for example, collodial silica, quartz, amorphous silica, glass, graphite, carbon black, titania, or the like) or different degrees of cross-linking in the synthetic polymers. Thus, the core may be comprised of an elastomer highly loaded with filler or highly cross-linked and thus hard and stiff. The outer component may be comprised of the same elastomer but with a much lower filler loading or lower degree of cross-linking and thus be more pliable and elastic than the core. A particular advantage of such a wedge is anticipated to be in ease of manufacture. Additionally, it is anticipated that problems noted with separation of the outer component from the core when different materials are used would be resolved as the core and outer component would form a continuum of the same material.

Figure 2:
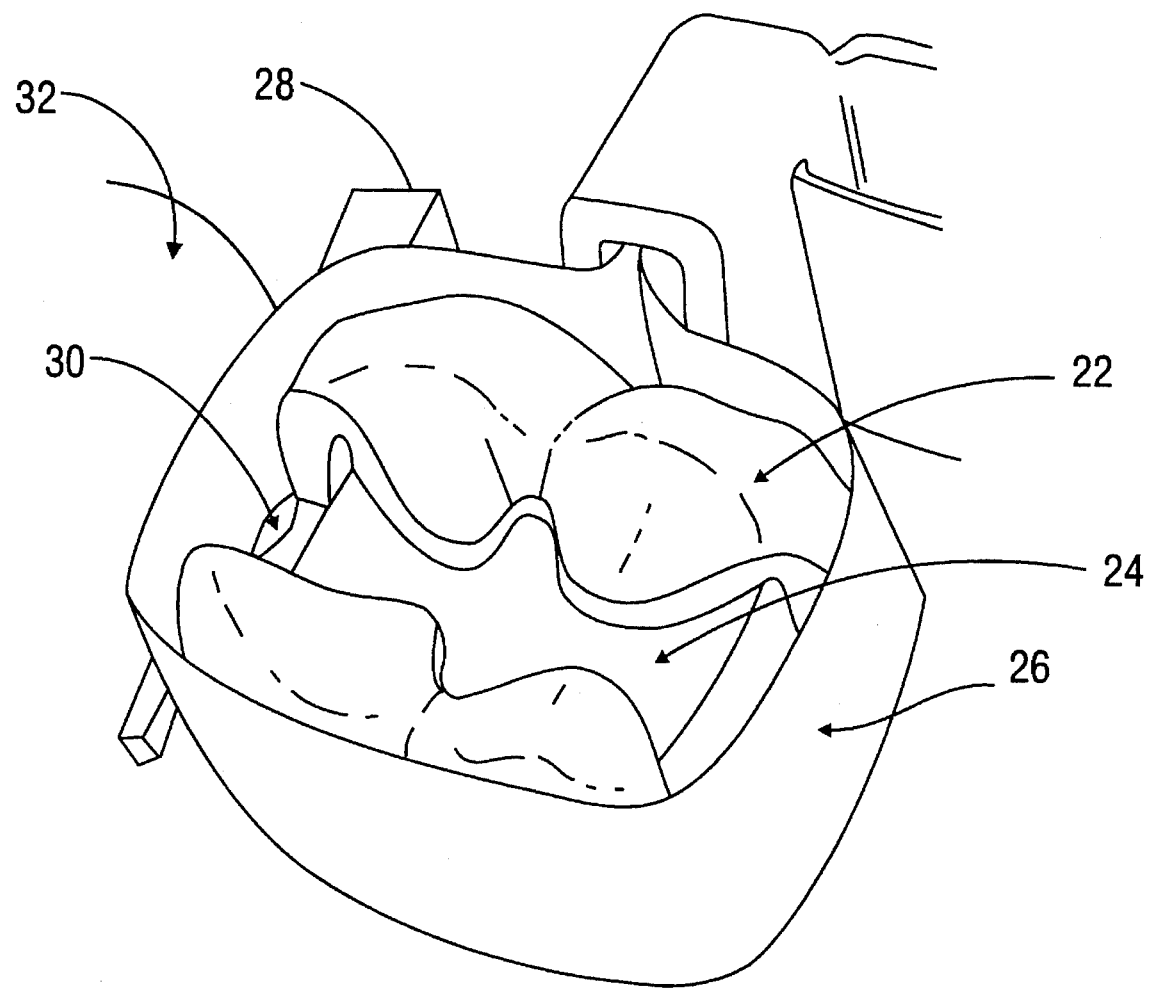
FIG. 2 is a perspective view of a mandibular molar tooth prepared for a class II restoration and possessing a concave defect in the left (distal) aspect of the preparation. The tooth is surrounded by a matrix band on a matrix retainer; and a dental wedge is seen in place between the prepared tooth and the adjacent tooth.

In use, a dental wedge is first placed between adjacent teeth, pointed end in first, and positioned to provide adequate separation. As is well known, the separation between the teeth is necessary to compensate for the thickness of a matrix band used in restorative dentistry. This use of a dental wedge is illustrated in FIG. 2. As is seen in FIG. 2, a molar tooth 22 has been prepared for a class II restoration 24. A matrix band 26 is placed around the tooth, and a dental wedge 28 is inserted in between the tooth and an adjacent tooth 32 to separate the teeth and conform and hold the matrix band against the tooth to be restored. A concave defect 30 exists on the side of the tooth.

Concavities are common in the interproximal root surfaces of posterior teeth. Irregularities of the interproximal surfaces of teeth may also exist due to decay or trauma to the tooth. Restoring these surfaces to proper form tends to be difficult or impossible with a fixed-geometry, hard wedge.

The dental wedge of the present invention makes restoring these surfaces much more practicable and predictable. After a wedge of the invention is forced into place, achieving desired tooth separation, the elastic outer component rebounds to conform to the concave defect in the side of the tooth. Thus, the two primary criteria for a dental wedge, adequate separation and conforming to the tooth's irregularities, are met. Further, because the outer component is elastic and can rebound into the tooth's irregularities, it will not tend to "back out." It appears that the elastic outer component offers greater traction against gum tissue as well.

While the wedges of the present invention work excellently as an aid to placing silver amalgam fillings ("amalgams"), the wedges are contemplated to be especially valuable in restoring posterior teeth with tooth-colored resin composite filling materials ("composites"). Achieving proper interproximal contacts has long been a problem when placing composites. This is because composite filling material is relatively fluid, especially when compared with silver amalgam. Consequently, the dentist cannot forcibly "pack" the composite filling material into the matrix-confined cavity space and achieve any further separation of the teeth as he may be able to with amalgam.

In addition, because composites are relatively fluid, the matrix band must be properly supported by the wedge; otherwise, the filling material may flow into irregularities and create ledges and overhangs. Because composites are tooth colored, it is much more difficult for a dentist to detect an overhang and correct it than when amalgam is used. Thus, with the aid of the dental wedge of the present invention, the dentist is able to more predictably place composite restorations, especially in posterior teeth, with proper interproximal contacts and anatomic contours.

As adjuncts to restorative dentistry, it is anticipated that the dental wedges of the present invention may be embodied in various ways to be most helpful to the dentist. In certain circumstances, it may be helpful and desirable to have a wedge that can be viewed on a radiograph, particularly in the unfortunate event of aspiration of a wedge by a patient. Both the core and the elastic component of the wedge of the invention may be made radiopaque by incorporating x-ray absorbing elements (i.e., high atomic number elements such as Ba, Bi, Ta, Sr, Zn, Zr or the like) into them.

Besides radiopacifying agents, both the core and the elastic component may contain coloring or identifying components. The core may be made with transparent materials and it may also contain a reflecting surface, if desired.

As the dental wedge of the present invention is thought to be very advantageous when restoring teeth with composites, both the core and elastic outer component can be made of transparent materials. Thus, with the use of a clear matrix band and a transparent wedge of the present invention, light cured composites can be predictably placed and cured with the wedge in place, something that cannot be done with an opaque wedge.

It is contemplated that wedges of the present invention, especially those wedges made with gel elastomer outer coverings, may find extensive use for the delivery of various medications to the gingiva in between teeth. For example, gel-clad wedges may be soaked in a hemostatic, antibiotic, or anti-inflammatory solution or a mixture thereof before use or when manufactured. It is contemplated that the medication-containing solution in which the wedges are soaked would be at least partially absorbed into the solvent phase of the gel and thus the gel would act as a depot for the medication.

A gel-clad wedge carrying a hemostatic agent appears to be an excellent adjunct to procedures requiring a dry field, for instance, when preparing and seating porcelain and other bonded restorations, or preparing and seating metal restorations. Often the interproximal gingiva is traumatized during such procedures and bleeds. The use of a hemostatic agent carrying, gel-clad wedge would help to reduce or stop the resulting bleeding and provide a dry field.

Generally, commercial dental wedges are provided in a great number of sizes. This is to account for the variation in the human dentition, where interdental spaces run from small to very large. Also, as would be expected, a child's dentition possesses smaller spaces between the teeth than those found in an adult's dentition. Consequently, a dentist is required to keep a wide variety of sizes of dental wedges on hand.

The dental wedge of the present invention typically has an enlarged cross-section in the body portion of the wedge due to the presence of the elastic outer component. The cross-section of the elastic outer component will generally reflect the shape of the underlying core because the outer component extends outward about 1 mm from the core. Because the outer component is compressible and elastic, it is not necessary for its cross-section to have a well-defined geometry. Consequently, it is anticipated that because the elastic outer component of the dental wedge of the invention is firm but compressible, the wedges may be made slightly larger in cross-section than presently available commercial wedges and fewer sizes of wedges of the invention will be required in the dentist's restorative armamentarium. That is, fewer sizes of the dental wedge of the present invention should be required to perform the same range of restorative tasks that presently require a wide variety of sizes of current commercially available wedges.

Early prototypes of the present invention were made by first preparing a mold-forming pattern by adding wax to a trimmed, plastic Cure-Thru™ wedge which is commercially available from ESPE-Premier, Norristown, Pa. Wax was added to the trimmed wedge to achieve the contours desired for the final wedge. This pattern was then used to make a rubber mold wherein a dental polyvinylsiloxane impression material of the addition-cured elastomer type, Express™ by 3M, was used. A trimmed, Cure-Thru™ wedge (without wax) was placed in the resulting rubber mold and a hydrogel-forming copolymer added and cured. The resulting prototype wedge had an enlarged cross-section following the tetrahedral contours of the core, consisting of hydrogel polymer at about the longitudinal middle. Finally, these wedges were washed extensively in water and stored in a hydrated state.

Later prototypes were made in a similar fashion, but using non-gel elastomers. A mold was made as described above and a rigid core cast from polymethyl methacrylate resin placed in the mold. Various non-gel elastomers were used in place of the hydrogel-forming copolymer, and cured. The twelve elastomers used were room temperature vulcanizing ("RTV") rubbers of silicone, polysulfide, and polyether. See Table 1 below.

TABLE 1

| Elastomer Type | Clear, Transparent, Opaque | Hardness (Durometer A) | Tested As Prototypes | Source |
| --- | --- | --- | --- | --- |
| Polyether | O | 60 | ✓ | Polygel NF |
| Polysiloxane | O | 85 | ✓ | Parkell Blue Mousse |
| Polysiloxane | O | 60 | ✓ | Parkell Green Mousse |
| Polysiloxane | O | 55 | ✓ | Reprosil |
| Polysiloxane | O | 60 | ✓ | Impregum |
| Polysiloxane | O | 60 | ✓ | 3M Express |
| Silicone | C | 55 | ✓ | Dow Corning Silastic 732 |
| Silicone | T | 27 | | Dow Corning MDX4 4210 Silastic |
| Silicone | C | 40 | | Dow Corning Sylgard 184 |
| Silicone | C | — | | 3M 442 encapsulant |
| Silicone | C | — | | 3M super sealant |
| Silicone | C | — | | 3M 4475 adhesive |
| Silicone | T | 25 | ✓ | G.E. RTV 118 sealant |
| Silicone | T | 45 | ✓ | G.E. RTV 615A rubber |
| Silicone | T | 15 | ✓ | G.E. RTV 12A potting compound |
| Polysulfide | O | 50 | ✓ | Neo-Plex |
| Polyethyl-methacrylate | O | 20 | ✓ | Lynal, L.D. Caulk Co. |

— = not measured

It is contemplated that wedges of the present invention may be fabricated on a commercial scale by bulk molding, injection molding, reaction injection molding, or extrusion methods. The elastic outer component may be comprised of either thermosetting or thermoplastic elastomeric materials.

The first prototype wedges made with hydrogel exteriors tended to be fragile due to imperfect adhesion of the hydrogel to the Cure-Thru™ wedge core. In an effort to improve those results, rigid cores were then fabricated from polymethyl methacrylate resin; and a hydrogel formulation [HPT-13: (HEMA 37.90% (w/w), HPMA 10.11%, TEGDMA 7.07%, dimethyl sulfoxide 44.47%, N,N-dihydroxyethyl-p-toluidine 0.61%, and benzoyl peroxide 0.61%)] cured over the core. These proved to be a promising improvement, but still tended to be fragile. The prototype wedges made with non-gel elastomer exteriors proved to be durable and were used for evaluation of the invention as described below.

Tests were performed using a fixture that directly measures a wedge's ability to conform to concave defects at the interproximal, gingival margin. The fixture consists of a typodont first molar tooth embedded in acrylic and a maxillary premolar typodont tooth embedded in an elastomer. The premolar is affixed to a sliding acrylic piece such that the premolar can repeatedly be brought to the exact location against the molar and held in place with a screw. The premolar was prepared with a class 2 cavity preparation and a small concavity was cut in the distal side to represent a convex defect. The test wedges were placed between these two teeth with a dead-soft, 0.02 mm metal band placed around the prepared tooth. The gap remaining between the matrix band and the distal surface at the defect was measured from photographic images.

Figure 3:
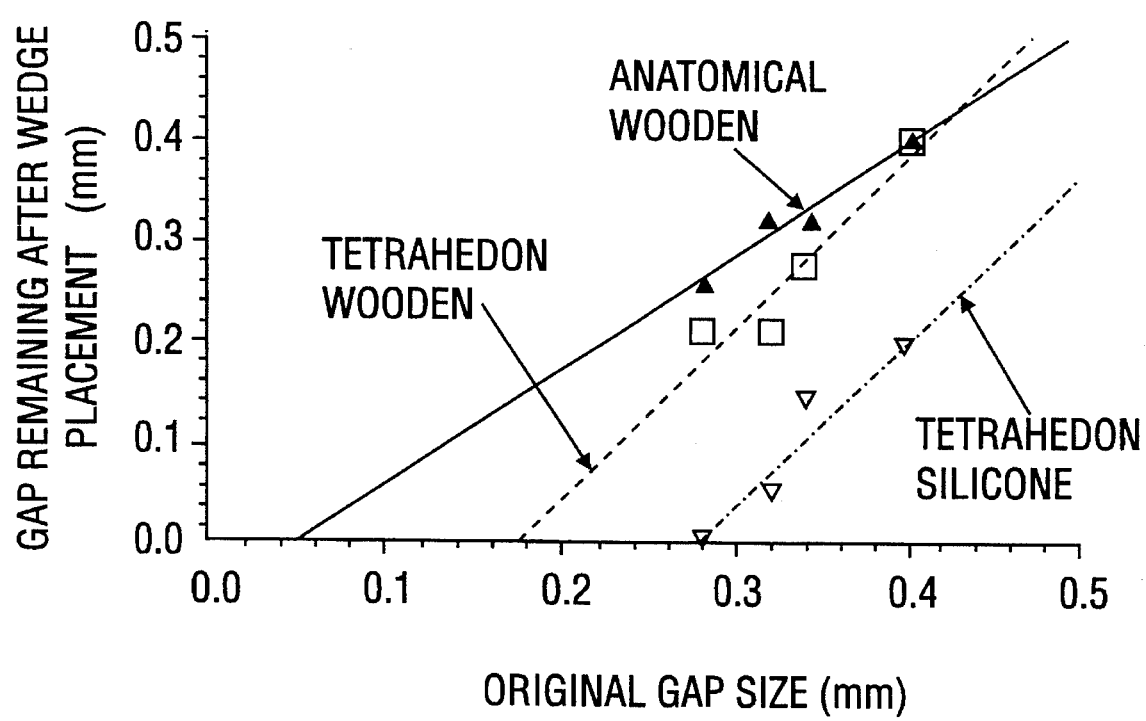
FIG. 3 is a chart comparing the performance of a wedge of the invention with two conventional wedges.

The results of the above tests, using two types of commercially produced wooden wedges and a prototype wedge with a polysiloxane (non-gel elastomer) exterior, are shown in FIG. 3. The prototype wedge used, possessed a polymethyl methacrylate core and a polysiloxane rubber exterior prepared from Reprosil™ light-body impression material. FIG. 3 shows that while the polysiloxane/polymethyl methacrylate core wedge completely closed a 0.28 mm gap, anatomically-carved wooden wedges failed to close this gap and are predicted to close only gaps smaller than about 0.05 mm. Similarly, a tetrahedral wooden wedge also did not close a 0.28 mm gap and is predicted to close only gaps smaller than about 0.18 mm.

Subsequent to the above experiments, a variety of rigid-core, non-gel elastomer-covered wedges were evaluated with the test fixture using a 0.40 mm defect. Of those materials listed in Table 1 as having been tested, four elastomer coverings completely closed the gap caused by the 0.40 mm defect:

Blue-Mousse™ polysiloxane, Parkell Inc.

Green-Mousse™ polysiloxane, Parkell Inc.

Express™ putty polysiloxane, 3M Co.

RTV 732 Silastic™ silicone, Dow Corning Co.

One other, General Electric's RTV 118™ adhesive sealant, left only a hairline gap. The others closed the gap to varying degrees. The more rigid elastomers gave the better results. Silicone rubbers offer significant promise for this application, but it is contemplated that other elastomers meeting the criteria of the invention will also prove effective.

Additional advantages and modifications will be readily apparent to those skilled in the art. The invention in its broader aspects is therefore not limited to the specific details or representative examples described. Accordingly, departures may be made from the detail without departing from the spirit or scope of the disclosed general inventive concept.

What is claimed is:

1. A dental wedge, comprising:

a rigid, substantially conical core; and an elastomeric outer component coupled to said rigid core to form a one-piece structure, said outer component being sufficiently elastic to conform to the contours of tooth surfaces.

2. The dental wedge of claim 1 wherein the outer component has a durometer-A hardness of at least about 50.

3. The dental wedge of claim 1 wherein said outer component comprises a gel elastomer.

4. The dental wedge of claim 1 wherein said outer component comprises a non-gel elastomer.

5. The dental wedge of claim 1 wherein said rigid core is radiopaque.

6. The dental wedge of claim 1 wherein said outer component is radiopaque.

7. The dental wedge of claim 1 which further comprises a medication dispensable from said outer component.

8. The dental wedge of claim 1 wherein said rigid core and said outer component are transparent.

9. The dental wedge of claim 1 wherein said rigid core is comprised of polymethyl methacrylate.

10. The dental wedge of claim 1 wherein said rigid core is comprised of a common elastomer and said outer component is comprised of a common elastomer.

11. A dental wedge, comprising:
a rigid, substantially conical core; and
an elastomeric outer component coupled to said rigid core to form a unitary structure, said outer component being sufficiently hard to cause separation between two teeth and sufficiently soft and elastic to conform to the interproximal surfaces of said teeth.

12. The dental wedge of claim 11 wherein said outer component is a gel elastomer.

13. The dental wedge of claim 11 wherein said outer component is a non-gel elastomer.

14. The dental wedge of claim 11 wherein said rigid core is radiopaque.

15. The dental wedge of claim 11 wherein said outer component is radiopaque.

16. The dental wedge of claim 11 wherein said rigid core and said outer component are transparent.

17. The dental wedge of claim 11 wherein said rigid core is comprised of a common elastomer and said outer component is comprised of a common elastomer.

18. The dental wedge of claim 11 which further comprises a medication dispensable from the outer component.

* * * * *